(12) United States Patent
Wischmann et al.

(10) Patent No.: US 9,649,082 B2
(45) Date of Patent: May 16, 2017

(54) DIFFERENTIAL PHASE CONTRAST IMAGING DEVICE WITH MOVABLE GRATING(S)

(71) Applicant: KONINKLIJKE PHILIPS N.V., Eindhoven (NL)

(72) Inventors: Hans-Aloys Wischmann, Henstedt-Ulzburg (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/438,947

(22) PCT Filed: Sep. 16, 2014

(86) PCT No.: PCT/EP2014/069644
§ 371 (c)(1),
(2) Date: Apr. 28, 2015

(87) PCT Pub. No.: WO2015/044001
PCT Pub. Date: Apr. 2, 2015

(65) Prior Publication Data
US 2015/0272528 A1    Oct. 1, 2015

(30) Foreign Application Priority Data

Sep. 30, 2013 (EP) .................................... 13186594
Jul. 17, 2014 (EP) .................................... 14177486

(51) Int. Cl.
*G01N 23/04* (2006.01)
*A61B 6/00* (2006.01)
(Continued)

(52) U.S. Cl.
CPC ................ *A61B 6/484* (2013.01); *A61B 6/06* (2013.01); *A61B 6/4035* (2013.01);
(Continued)

(58) Field of Classification Search
None
See application file for complete search history.

(56) References Cited

U.S. PATENT DOCUMENTS 5,812,629 A *   9/1998   Clauser ................. A61B 6/032
                                                      378/37
6,573,997 B1 *  6/2003   Goldberg ........... G01M 11/0264
                                                      356/515
(Continued)

FOREIGN PATENT DOCUMENTS

DE    WO 2013111050 A1 *  8/2013   ............. A61B 6/484
SE    WO 2013004574 A1 *  1/2013   ........... A61B 6/4035
(Continued)

OTHER PUBLICATIONS

Zhao, Wu et al, "A new method to retrieve phase information for equiangular fan beam differential phase contrast computed tomography", Medical Physics, AIP, Melville, NY, U.S., vol. 40, No. 3, Feb. 25, 2013, pp. 31911-1 to 31911-8, XP012171051, ISSN: 0094-2405, DOI: 10.1118/1.4791672.

*Primary Examiner* — Andrew Smyth

(57) ABSTRACT

An X-ray differential phase contrast imaging device (10) comprises an X-ray source (20) for generating an X-ray beam; a source grating (G0) for generating a coherent X-ray beam from a non-coherent X-ray source (20); a collimator (22) for splitting the coherent X-ray beam into a plurality of fan-shaped X-ray beams (28) for passing through an object (14); a phase grating (G1) for generating an interference pattern and an absorber grating (G2) for generating a Moiré pattern from the interference pattern arranged after the object (14); and a line detector (24) for detecting the Moiré pattern generated by the phase grating (G1) and the absorber grating (G2) from the fan-shaped X-ray beams (28) passing through the object (14). The X-ray source (20), source grating (G0), collimator (22), phase grating (G1), absorber grating (G2) and line detector (24) are fixed to a common
(Continued)

gantry (12) and are movable with respect to the object (14), such that a number of interference pattern from different positions of the gantry are detectable for reconstructing a differential phase image of the object (14). At least one grating (G0, G1, G2) comprises, in an alternating manner, groups (36) of grating lines (34) and transparent areas (38). At least one grating (G0, G1, G2) is movable with respect to the gantry (12), such that in a first position of the grating (G1, G2) the fan-shaped X-ray beams (28) pass through the grating lines (34), and in a second position of the grating (G1, G2), the fan-shaped X-ray beams (28) pass through the transparent areas (38).

15 Claims, 4 Drawing Sheets

(51) Int. Cl.
  *A61B 6/06* (2006.01)
  *A61B 6/03* (2006.01)
  *G21K 1/02* (2006.01)
  *G21K 1/06* (2006.01)
(52) U.S. Cl.
  CPC .......... *A61B 6/4078* (2013.01); *A61B 6/4208* (2013.01); *A61B 6/4291* (2013.01); *A61B 6/4435* (2013.01); *A61B 6/585* (2013.01); A61B 6/03 (2013.01); A61B 6/502 (2013.01); A61B 6/547 (2013.01); G21K 1/025 (2013.01); G21K 1/06 (2013.01); G21K 2207/005 (2013.01)

(56) References Cited

U.S. PATENT DOCUMENTS

| | | | | |
|---|---|---|---|---|
| 7,693,256 B2 * | 4/2010 | Brahme | ................ | A61B 6/022 378/41 |
| 7,889,838 B2 * | 2/2011 | David | ................ | A61B 6/4233 378/36 |
| 8,855,265 B2 * | 10/2014 | Engel | ................ | A61B 6/00 378/36 |
| 2004/0131145 A1 * | 7/2004 | Ohara | ................ | A61B 6/0414 378/37 |
| 2009/0092227 A1 * | 4/2009 | David | ................ | A61B 6/4233 378/36 |
| 2009/0238334 A1 * | 9/2009 | Brahme | ................ | A61B 6/022 378/41 |
| 2009/0316857 A1 * | 12/2009 | David | ................ | A61B 6/484 378/62 |
| 2011/0070488 A1 | 3/2011 | West et al. | | |
| 2011/0142316 A1 * | 6/2011 | Wang | ................ | G06T 11/006 382/131 |
| 2012/0028379 A1 * | 2/2012 | Dhindsa | ............ | H01J 37/3244 438/14 |
| 2012/0099702 A1 * | 4/2012 | Engel | ................ | A61B 6/00 378/62 |
| 2012/0128126 A1 * | 5/2012 | Ishii | ................ | A61B 6/4291 378/62 |
| 2012/0155610 A1 * | 6/2012 | Murakoshi | ........... | A61B 6/4291 378/62 |
| 2012/0236992 A1 * | 9/2012 | Engel | ................ | A61B 6/00 378/62 |
| 2012/0243658 A1 * | 9/2012 | Geller | ................ | A61B 6/00 378/16 |
| 2012/0307966 A1 * | 12/2012 | Roessl | ................ | A61B 6/00 378/16 |
| 2013/0202081 A1 * | 8/2013 | Rossl | ................ | A61B 6/484 378/36 |
| 2013/0230135 A1 * | 9/2013 | Hoshino | ................ | A61B 6/04 378/36 |

FOREIGN PATENT DOCUMENTS

| | | |
|---|---|---|
| WO | 2011070488 A1 | 6/2011 |
| WO | 2013004574 A1 | 1/2013 |
| WO | 2013111050 A1 | 8/2013 |

* cited by examiner

DIFFERENTIAL PHASE CONTRAST IMAGING DEVICE WITH MOVABLE GRATING(S)

CROSS-REFERENCE TO PRIOR APPLICATIONS

This application is the U.S. National Phase application under 35 U.S.C. §371 of International Application No. PCT/EP2014/069644, filed on Sep. 16, 2014, which claims the benefit of European Patent Application Nos. 13186594.1, filed on Sep. 30, 2013 and 14177486.9, filed on Jul. 17, 2014. These applications are hereby incorporated by reference herein.

FIELD OF THE INVENTION

The invention relates to the field of differential phase contrast imaging (dPCI). In particular, the invention relates to a device and a method for X-ray differential phase contrast imaging and X-ray attenuation imaging.

BACKGROUND OF THE INVENTION

X-ray differential phase contrast imaging (dPCI) visualizes the phase information of coherent X-rays passing through a scanned object. For example, the coherent X-rays may be generated by a source grating between an incoherent X-ray source and the scanned object. In addition to classical X-ray attenuation imaging, dPCI may determine not only the absorption properties of the object along a projection line, but also the phase-shift of the transmitted X-rays. After the object, a phase-shifting grating (also known as phase grating) is placed, which generates an interference pattern that contains the required information about the beam phase-shift in the relative position of its minima and maxima, typically in the order of several micrometers. Since a common X-ray detector may not be able to resolve such fine structures, the interference pattern is sampled with an analyzer grating (also known as absorber grating), which features a periodic pattern of transmitting an absorbing strip with a periodicity similar to that of the interference pattern. The similar periodicity produces a Moiré pattern behind the grating with a much larger periodicity, which is detectable by a common X-ray detector.

For performing dPCI there exist essentially two different system geometries: planar 2D detection and slit-scanning systems.

In planar 2D detection, a 2D detector array takes an entire projection image in a single X-ray exposure and the phase acquisition has to be realized by a process called "phase-stepping" with, for example, 4, 8 or 16 exposures, in which one of the source grating, the phase grating and the absorber grating is moved relative to the other two gratings.

In the slit scanning approach, the woman's breast is scanned by a scan arm or gantry movement below the breast. The redundancy of the data acquisition by means of a typical arrangement of a number of parallel detector lines can be exploited to eliminate the need for phase-stepping and the gratings need not be moved with respect to each other. Hence, the phase-acquisition can be implemented in the ordinary scanning motion, as, for example described in WO2013/004574A1.

However, in both cases, the differential phase contrast technique, characterized by its use of three gratings, has the disadvantage that approximately 50% of the X-rays that have passed through the breast tissue are actually absorbed by the absorber grating and thus are lost for imaging or are not used for imaging.

Sometimes it may be desirable to perform not only dPCI imaging but instead or in addition attenuation imaging without gratings. For example, W2012/0099702 A1 shows a differential phase contrast imaging device with a movable grating.

Calibration of the detector and dPCI system may be difficult, if the gratings cannot be removed, and calibration e.g. for drift or other detector performance changes may be required more than just at the factory/initial installation but on a regular basis, and at least after every maintenance.

WO 2013/111050 A1 discloses an x-ray system provided with grating structures, such grating structures comprising sets of slits, which sets have mutually different directions.

U.S. 2013/0202081 A1 discloses a detector arrangement for phase contrast imaging comprising movable gratings.

US 2013/0230135 A1 discloses a joint imaging apparatus comprising gratings.

WO 2011/070488 A1 discloses a device for phase contrast imaging comprising a grating being movable out of the X-ray beam.

SUMMARY OF THE INVENTION

In a 2D detection system, the absorber grating covers the entire detection area and has to be removed from the entire field-of-view (up to about 30 cm×40 cm), i.e. over a rather long distance. This may result in a bad alignment of the absorber grating and the phase grating after the movement and may degrade the image quality. Additionally, the preferred movement direction in a 2D mammographic system would be the anterior-posterior direction, shifting the absorber grating out of the X-ray imaging path away from the breast.

There may be a need to provide an X-ray imaging device that is able to easily switch between pure attenuation imaging and dPCI imaging (while providing attenuation, differential phase and scatter imaging) There also may be need to provide a device that is fast, simply, accurately and reliably switched between these two operation modes.

These needs may be met by the subject-matter of the independent claims. Further exemplary embodiments are evident from the dependent claims and the following description.

An aspect of the invention relates to an X-ray differential phase contrast imaging device, for example to a mammography device.

According to an embodiment of the invention, the imaging device comprises an X-ray source for generating an X-ray beam; a source grating (G0) for generating a coherent X-ray beam from a non-coherent X-ray source (20); a collimator comprising slits for splitting the coherent X-ray beam into a plurality of fan-shaped X-ray beams for passing through an object; a phase grating and an absorber grating arranged after the object; and a line detector comprising detector lines for detecting a Moiré pattern generated by the phase grating and the absorber grating from the fan-shaped X-ray beams passing through the object. The X-ray source, source grating, collimator, phase grating, absorber grating and detector are fixed to a common gantry and are movable with respect to the object, such that a number of interference patterns from different positions of the gantry are detectable for reconstructing a differential phase image of the object. At least one grating of the source grating, phase grating and the absorber grating comprises groups of grating lines and transparent areas between the groups of grating lines. Herein, the groups of grating lines and the transparent areas alternate with respect to each other in a direction perpendicular to the direction of the detector lines. At least one grating of the source grating, phase grating and the absorber grating is movable with respect to the gantry, such that: in a first (dPCI) position of the source grating the X-ray beams pass through the grating lines and subsequently pass through the slits of the collimator, and in a second (attenuation imaging) position of the source grating, the X-ray beams pass through the transparent areas and subsequently pass through the slits of the collimator, or, in a first position at least one of the phase grating or the absorber grating the fan-shaped X-ray beams pass through the grating lines, and in a second position at least one of the phase grating or the absorber grating the fan-shaped X-ray beams pass through the transparent areas.

Therefore, since the groups of grating lines and transparent areas alternate with respect to each other in a direction perpendicular to the detector lines, in the first position the groups of grating lines project onto the spaces between neighboring detector lines (i.e. the spaces between neighboring detector lines in a direction perpendicular to the direction of the detector lines), whereas in the second position the transparent areas project onto such spaces. Consequently, the X-ray differential phase contrast imaging device according to the invention effectively utilizes the spaces between neighboring detector lines thereby enabling switching from dPCI imaging to attenuation imaging (and from attenuation imaging to dPCI imaging) while circumventing the need to move one or more of the grating(s) out of the X-ray field of view entirely (and the need to move said one or more of the grating(s) into the X-ray field of view, respectively).

In a slit scanning device, only the areas of the phase grating and/or absorber grating, which are exposed to X-rays need to have grating lines. The other areas may be made or left transparent to X-rays.

In the configuration with all gratings in a position such that the slits are aligned with the grating lines of the gratings, the imaging device is adapted to generate dPCI data, which usually contains information about attenuation, differential phase and scatter of X-rays in the object.

When it is desired to make a (pure) attenuation image, the phase grating and/or the absorber grating may be moved into a position, such that they are exposed to X-rays at areas transparent to X-rays without grating lines. In such a way, the attenuation of the gratings during the (pure) attenuation imaging and the X-ray dose delivered to the object (which may be a patient) may be reduced.

The phase grating and the absorber grating may be seen as an interferometer of the imaging device, which may be seen as a slit scanning device with a retractable interferometer that allows switching between phase contrast and conventional imaging (mammography). This is achieved by removing (and introducing) the areas with grating lines from the setup. For example, the absorber grating may have a silicon wafer as substrate comprising (50%) absorbing portions (trenches in the wafer filled with gold for forming the grating lines) and transparent areas (plain silicon). An on-off mechanism may be realized by a lateral shift of the absorber grating over a relatively small distance.

Contrary to this, in planar 2D detection such as in full-field digital mammography (FFDM), the phase grating and/or absorber grating have to be completely removed from/reinserted into the X-ray field-of-view entirely, over a larger distance.

A further aspect of the invention relates to a method for acquiring differential phase image data and attenuation image data with the same device, which may be an image device as described in the above and in the following.

According to an embodiment of the invention, the method comprises: moving a grating selected from a phase grating and an absorber grating of the device in a first position, such that the fan-shaped X-ray beams generated by a collimator can pass through groups of grating lines on the grating; acquiring differential phase image data by moving a gantry with the phase grating and absorber grating and a line detector with respect to an object and by detecting X-rays passing through the object, the phase grating and the absorber grating at a plurality of positions of the gantry; moving the grating in a second position, such that the fan-shaped X-ray beams can pass through transparent areas on the grating; and acquiring (pure) attenuation image data by moving the gantry with respect to the object and by detecting X-rays passing through the object at a plurality of positions of the gantry.

For example, by simply moving the absorber grating and/or the phase grating by a relative small distance, differential phase imaging may be switched to (pure) attenuation imaging.

In mammography, depending on the clinical application, certain parts of the mammography workload will benefit from the differential phase imaging. However, part of the workload may still be carried out in conventional mode (attenuation imaging only). A clinician may desire to choose between modes on a per-patient (or even per-view) basis.

These and other aspects of the invention will be apparent from and elucidated with reference to the embodiments described hereinafter.

BRIEF DESCRIPTION OF THE DRAWINGS

The reference symbols used in the drawings, and their meanings, are listed in summary form in the list of reference symbols. In principle, identical parts are provided with the same reference symbols in the figures.

DETAILED DESCRIPTION OF EMBODIMENTS

Figure 1:
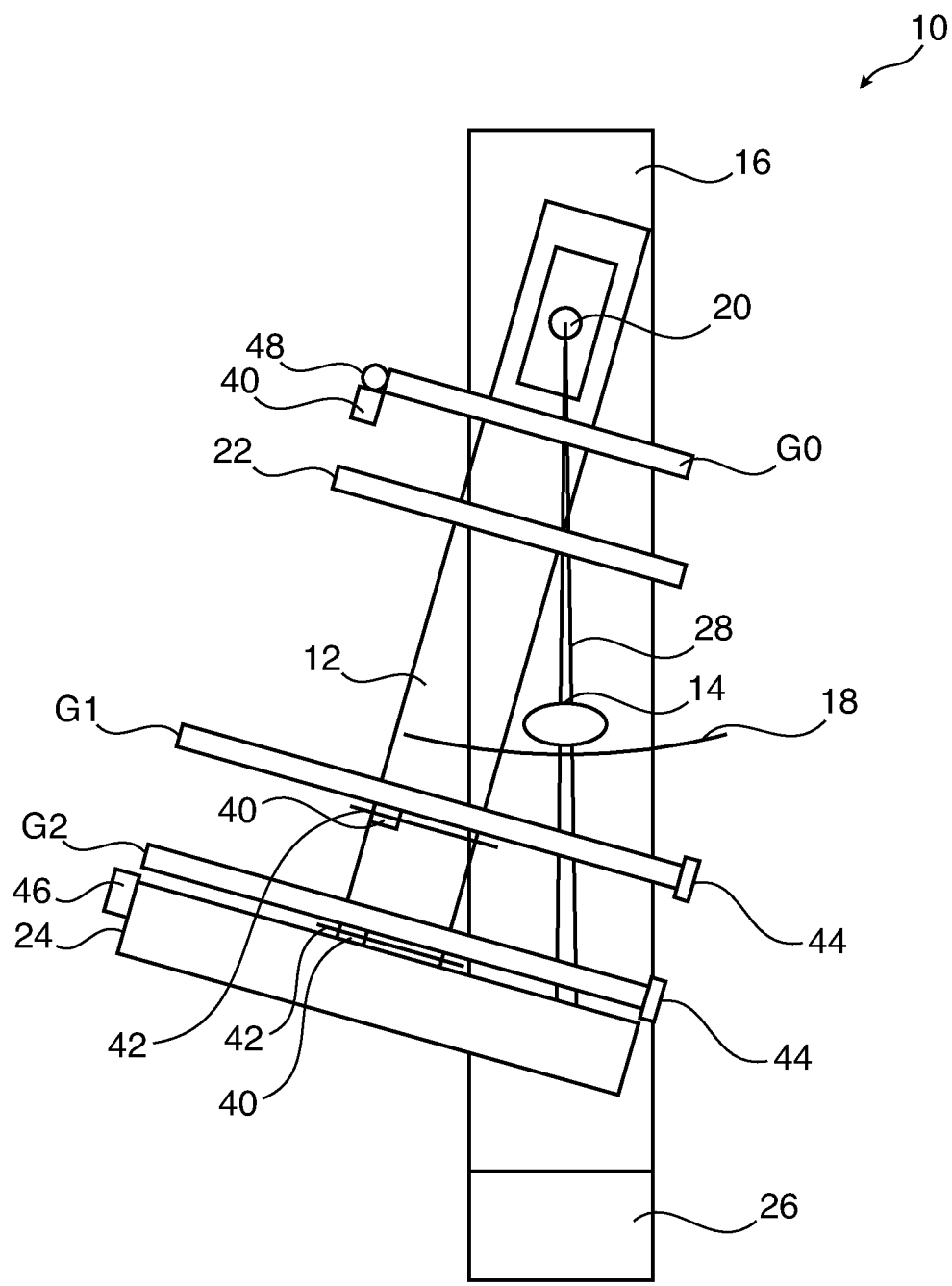
FIG. 1 schematically shows an imaging device according to an embodiment of the invention.

FIG. 1 shows an X-ray imaging device 10 with a movable gantry 12 that is movable in an angular range with respect to an object 14. The X-ray imaging device 10 may be a mammography device and the object 14 may be a woman's breast that is supported on a support platform 18 fixed to the device 10, for example to a frame 16 also carrying the gantry 10.

The gantry 10 carries an X-ray source 20 (for example an X-ray tube), a source grating G0, a collimator 22, a phase grating G1, an absorber grating G2, and a line detector 24.

The gratings G0, G1, G2, the collimator 18 and the line detector 24 are attached to the gantry 10 at fixed distances with respect to the X-ray source 16.

For acquiring image data, a controller 26 of the device 10 moves the gantry 12 in an angular range around the object 14 and acquires a number of projection images with the line detector 24 at different positions along the angular range.

A coherent X-ray beam generated by the source grating G0 from the (non-coherent) X-ray beam of the X-ray source 20 is split into fan-shaped beams 28 (one of which is indicated in FIG. 1) by the collimator 22.

Figure 2:
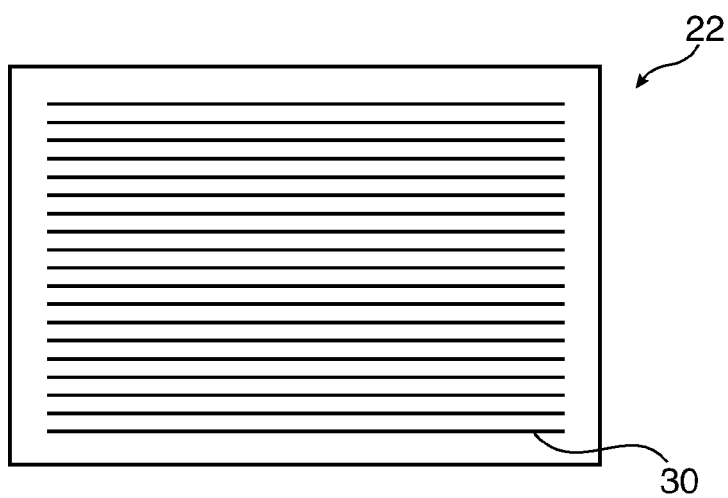
FIG. 2 schematically shows a collimator for an imaging device according to an embodiment of the invention.

The collimator 22 is shown in FIG. 2. It comprises a substantially rectangular substrate with a plurality of parallel equidistant slits 30. Usually, the longer sides of the collimator 22 are substantially parallel to the axis of movement of the gantry 12.

Figure 3:
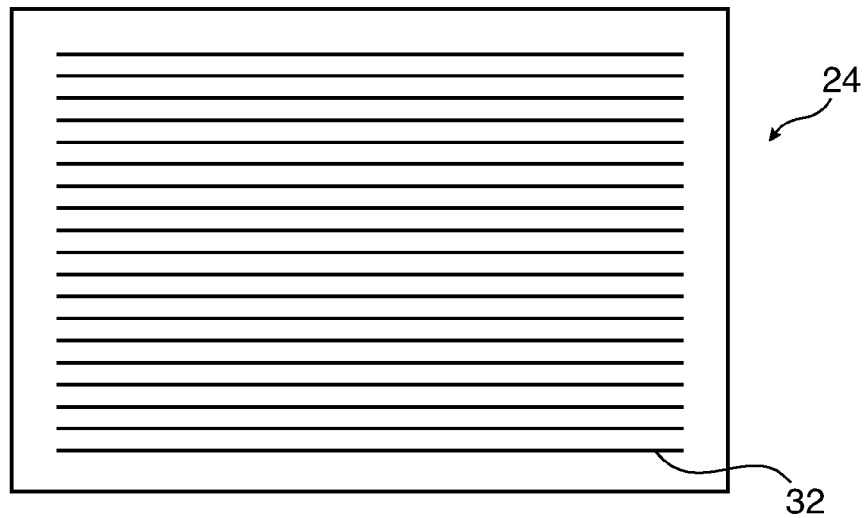
FIG. 3 schematically shows a line detector for an imaging device according to an embodiment of the invention.

Returning to FIG. 1, the fan-shaped beams 28 pass through the object 14 and the gratings G1, G2 and fall onto the line detector 24, which is shown in FIG. 3. Also the detector 24 comprises a substantially rectangular shape (seen from the X-ray source 20), wherein the longer sides are usually substantially orthogonal to the axis of movement of the gantry. The detector 24 comprises the same number of detector lines 32 as the collimator comprises slits 30. The detector lines 32, each of which comprises a line of pixel detector elements, are aligned with the slits 30, such that each fan-shaped X-ray beam 28 passing through the slits 30 falls on the respective line detector 32. The slit arrangement and/or arrangement of detector lines 32 may be more complicated than shown in the figures. Slits 30 and/or detector lines 32 may not go through in one piece (otherwise there would not be the need for several slits) and they might be slightly offset.

The controller 26 may evaluate the acquired image data and the interference pattern encoded therein, and may determine/reconstruct an image indicating the phase shifts of the object 16.

Figure 4:
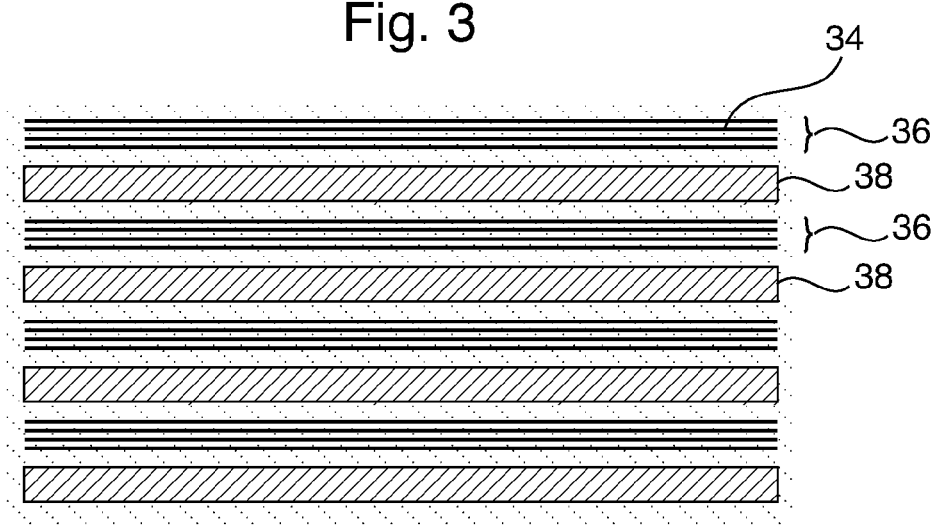
FIG. 4 schematically shows a part of a grating for an imaging device according to an embodiment of the invention.

A possible embodiment of the gratings G0, G1 and G2 is shown in FIG. 4. FIG. 4 shows a section of one of the gratings G0, G1, G2. Since only the components of the X-ray beam that in the end fall onto the detector need to be diffracted by the gratings, only the areas of the gratings G0, G1 and G2 need to have grating lines 34 that are in the way of the fan-shaped beams 28. Thus, the grating lines 34 may be grouped in groups 36 of grating lines 34 separated by areas without grating lines between them.

However, it is also possible that the only one or only two of the gratings are designed like shown in FIG. 4 and that the other gratings have grating lines over its whole area, which in particular may be the case for the source grating G0.

Since the diffraction gratings G0, G1 and G2 attenuate the X-ray beam more or less (at least by the area of the grating lines 34), it may be beneficial to remove them from the X-ray beam, when acquiring attenuation imaging data with the line detector 24.

In the embodiment shown in FIG. 1, this is realized with areas 38 (see FIG. 4) transparent to X-rays provided in the gratings G1 and G2. By laterally moving the gratings G1 and/or G2, the gratings may be moved from an "on"-position, in which the X-ray beams 28 run through the groups 36 into an "off"-position, in which the X-ray beams 28 run through the transparent areas 38.

According to an embodiment of the invention, at least one grating of the phase grating G1 and the absorber grating G2 comprises groups 36 of grating lines 34 and transparent areas 38 between the groups of grating lines and is movable with respect to the gantry 12, such that in a first "on"-position of the grating, the fan-shaped X-ray beams 28 pass through the grating lines 34, and in a second "off"-position of the grating, the fan-shaped X-ray beams 28 pass through the transparent areas 38.

Note that the direction of the grating lines 34 may be substantially normal to the plane of FIG. 1, i.e. that the grating lines may run substantially orthogonal to the movement direction of the gratings G0 and G1.

The transparent areas 38 are usually substantially rectangular. The smaller side of the rectangle may be much longer than the distance between two neighboring grating lines 34. Due to the equidistant slits 30 of the collimator 22, the groups 36 and the areas 38 may alternate and may all have the same distances from each other.

According to an embodiment of the invention, the groups 36 of grating lines 34 and the transparent areas 38 alternate with respect to each other.

According to an embodiment of the invention, the groups 36 of grating lines 34 are equidistant and the transparent areas 38 are equidistant.

Usually, the gratings G0, G1 and G2 are manufactured by etching a wafer (substrate) and/or putting a structured metallization on at least one side of the wafer. For example, the wafer may be a thin silicon wafer (300 mu-500 mu thick), which is substantially transparent to X-rays. The grating lines 34 of the gratings G0, G2 may be gold filled silicon trenches that absorb substantially 50% of the radiation impinging orthogonal to the grating G0, G2. The grating lines 34 of the phase grating G1 may be (empty) trenches in the substrate.

According to an embodiment of the invention, the grating lines may be metal lines on the substrate and/or may be or may comprise trenches in the substrate.

The transparent areas 38 may be provided with unprocessed parts of the substrate/silicon wafer, for example parts with no gold and no trenches at all.

According to an embodiment of the invention, at least one of the gratings G0, G1, G2 comprises a substrate transparent for X-rays and the transparent areas 38 are areas on the substrate without metallization.

However, it is also possible that the transparent areas 38 are provided by holes in the substrate.

According to an embodiment of the invention, the transparent areas 38 may be or may comprise holes in a substrate of the grating.

As further indicated in FIG. 1, grating G0 may be removed from the X-ray beam 28 with another method. The grating G0 may be attached to a hinge 48 and may be flapped out of the optical path of the X-rays 28, for example with a motor 40 controlled by the controller 26. However, it also may be possible that trenches of G0 are filled with liquid metal that may be emptied.

According to an embodiment of the invention, the imaging device 10 further comprises a hinge 48 for removing the source grating G0 from the X-ray beam.

The other two gratings G1 and G2 may be moved linearly by a (further) motor 40 controlled by the controller 26.

According to an embodiment of the invention, the device 10 comprises a motor 40 for moving at least one of the gratings G1, G2 between the first position and the second position, wherein a controller 26 controls the movement.

The motion may be implemented by a stepper motor, a belt-drive, or similar, provided the "on" end-point is mechanically robust and well-defined.

Since the "in-line" setting requires a very accurate alignment of the gratings G1, G2, the distance of mechanical movements may have to be limited in order to preserve accuracy. Similarly, G2 may have to be moved out or in within seconds, in order to not disrupt the workflow.

The positioning of the gratings G1 and G2 particularly in the first "on"-position (dPCI mode) usually must be well-defined as alignment of the gratings G1, G2 when employing dPCI is critical. Therefore, means may be required for ensuring a high mechanical precision in the "on"-position.

The device 10 may comprise a two-state switching mechanism 40, 44, with a geometrically very well-defined, lockable "on"-position and a geometrically more laxly defined "off"-position. The former would take the much higher precision into account with which the gratings G2 would have to be placed relative to G1 once phase contrast is required. The required accuracy may be ensured for example by a rigid mechanical stopper, or by an optical detection of the position of grating G2 at the "on"-position with a sensor 46. The accuracy needs to be sufficient to eliminate the need for a new calibration.

According to an embodiment of the invention, the first position of the grating G1, G2 is determined by a mechanical stopper 44.

According to an embodiment of the invention, the first position of the grating G1, G2 is determined by a position sensor 46.

If G1 stays fixed, and only G2 is mobile, the accurate locked position and/or motion end point for the dPCI mode may be ensured by measuring the Moiré pattern, i.e. an air image, while shifting G2 back, until it is again in the calibrated position and then stopping the motor.

Teflon rails 42 or similar may be provided as guides for the gratings G1, G2 in the other spatial directions vertical and other in-plane axis, without creating a risk of dust/residue that would accumulate on the detector or on the gratings G1, G2.

According to an embodiment of the invention, the imaging device 10 further comprises Teflon rails 42 for guiding the grating.

Usually, only the absorber grating G2 substantially influences the effective detective quantum efficiency of the device 10, i.e. the absorption of X-rays. The source grating G0, which may be located at the exit window of the X-ray source 20 and hence in front of the object, 14 influences only the available X-ray flux, not the dose. The phase grating G1, despite being behind the breast exerts only a small influence on the dose, as G1 is usually by design a phase-grating with small attenuation of only about 5-10%. Hence, switching from phase contrast to conventional imaging may be realized by removing only the absorber grating G2 from the setup, i.e. from the post-object X-ray imaging path.

According to an embodiment of the invention, only the absorber grating G2 has the transparent areas 38 and/or may be moved between the first position and the second position.

However, it is also possible to provide the phase grating G1 with transparent areas and to shift it for moving the transparent areas 38 in the optical path of the fan-shaped X-ray beams 38.

According to an embodiment of the invention, the phase grating G1 and the absorber grating G2 have the transparent areas 38 and/or may be moved between the first position and the second position.

As shown in FIG. 1, both gratings are moved by a respective motor 40 on a respective rail 42, i.e. they are movable independently from each other.

According to an embodiment of the invention, the phase grating G1 and the absorber grating G2 are movable independently from each other between the first position and the second position. There may be a first motor 40 for moving the phase grating G1 and a second motor for moving the absorber grating G2.

Figure 5:
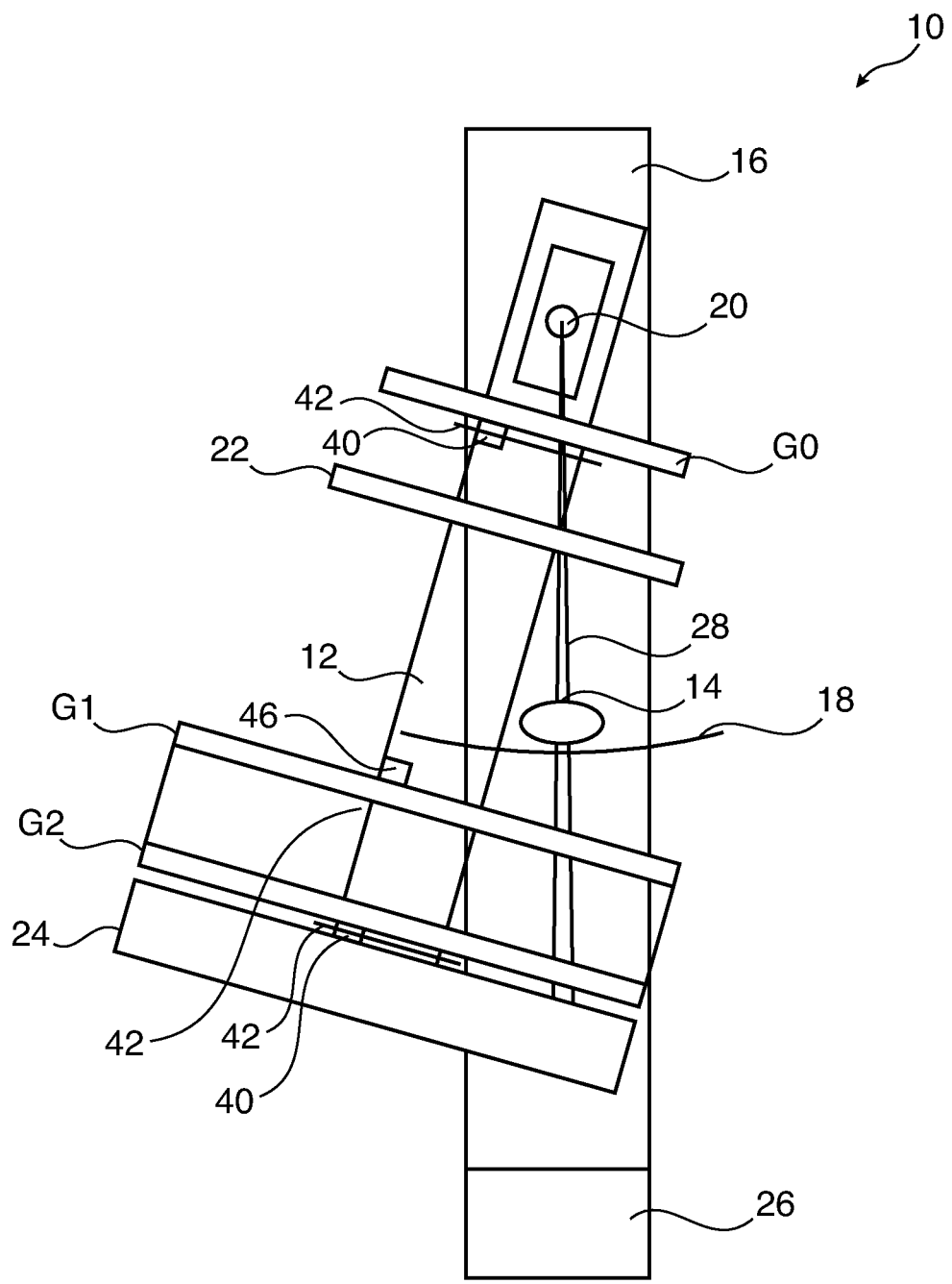
FIG. 5 schematically shows an imaging device according to a further embodiment of the invention.

FIG. 5 shows further possible embodiments, how the gratings G0, G1 and G2 may be moved. In FIG. 5, the gratings G1 and G2 are connected with each other, for example with a common frame and cannot move relative with each other, which may enhance the accurate alignment of the two gratings G1, G2.

According to an embodiment of the invention, the phase grating G1 and the absorber grating G2 are fixedly connected with each other and are movable together between the first position and the second position. The whole interferometer for dPCI, which comprises the two gratings G1, G2 may be retractable.

The movement may be performed with a common motor 40 controlled by the controller 26.

Furthermore, FIG. 5 shows that the grating G0 (when movable) may be moved like the gratings G1 and G2 shown in FIG. 5. In particular, the grating G0 may comprise groups 36 of grating lines 34 and may be laterally shifted by a motor 40 on a rail 42.

According to an embodiment of the invention, the source grating G0 comprises groups 36 of grating lines 34 and a transparent area 38 between the groups of grating lines and is movable with respect to the gantry 12, such that in a first position of the source grating G0, X-ray beams from the groups of grating lines pass through slits 30 in the collimator 22, and in a second position of the source grating G0, X-ray beams from transparent areas in the source grating pass through the slits 30 in the collimator 22.

According to an embodiment of the invention, the device 10 comprises a motor for moving the source grating G0 and/or a Teflon rail 42 for guiding the source grating G0. The movement of the grating lines of the source grating G0 out of the optical path may also enhance the speed of acquisition. When the source grating is not attenuating the X-ray beams, there may be 3 to 4 times more X-ray flux and the scan time may be much shorter for the same image quality.

Figure 6:
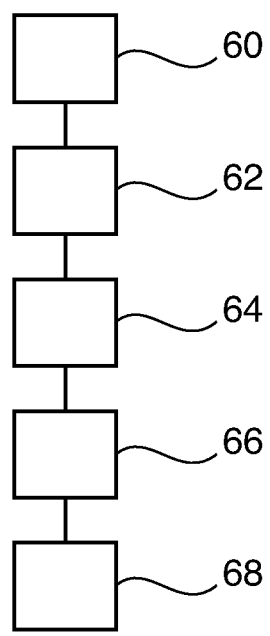
FIG. 6 shows a flow diagram for a method for acquiring dPCI and attenuation image data according to an embodiment of the invention.

FIG. 6 shows a method for acquiring differential phase image data and attenuation image data with the device 10 shown in FIG. 1 or 5.

In the beginning, it is assumed that the device 10 and the gratings G0, G1, G2 are in the "off"-position, i.e. the second position, in which the X-ray beams 28 may pass through areas 38 in one or more of the gratings G0, G1, G2. Furthermore, grating G0 may be flapped out of the optical path of the X-ray beams 28 by the hinge 48 (see FIG. 1).

In step 60, it is decided that dPCI data should be acquired. For example, a clinician using the device 10 may input a corresponding command into the controller 26.

The controller 26 moves the gratings G0, G1, G2 into the "on"-position (first position), when they are movable, for example by a lateral shift of the grating by a distance corresponding to a distance less than half the distance between two detector lines 32.

As the distance between two adjacent slits 30 of the collimator 22 is typically many multiples of a detector width of a single pixel in a device 10 with one pixel per line-width, it is easy to fabricate gratings G0 and/or G2 with Au filled silicon trenches only where needed while leaving adjacent areas metal-free.

For example, the gratings (or one or two of the gratings) may be moved by a distance equal to the distance between a group 36 of grating lines 34 and a neighboring transparent area 38.

According to an embodiment of the invention, at least one grating, two of the gratings or all of the gratings G0, G1, G2 of the device 10 are moved in a first position; such that fan-shaped X-ray beams 28 generated by a collimator 22 can pass through groups 36 of grating lines 34 on the grating.

The correct positioning of the gratings G0, G1, G2 after the movement may be controlled by mechanical stoppers 44 and/or by a sensor 46, which data is evaluated by the controller 26. Furthermore, the gratings G1, G2 may be moved independently from each other (FIG. 1) or may be moved with a common frame (FIG. 2).

In step 62, differential phase image data is acquired by moving the gantry 12 with the phase grating G1 and absorber grating G2 and the line detector 24 with respect to the object 14 and by detecting X-rays passing through the object 14, the phase grating G1 and the absorber grating G2 at a plurality of positions of the gantry 12.

The controller 26 may control the movement of the gantry 12 and furthermore may evaluate the acquired data from the line detectors 24 to generate the differential phase contrast image data.

In step 62, it is decided that pure attenuation image data should be acquired with the device 10. Also this command may be input by a clinician into the controller 26. The gratings G0, G1, G2 (if movable) are moved back into the "off"-position, i.e. the second position.

According to an embodiment of the invention, at least one of the gratings G0, G1, G2 are moved in the second position, such that the fan-shaped X-ray beams 28 can pass through transparent areas 38 on the grating G0, G1, G2.

In step 64, attenuation image data is acquired by moving the gantry 12 with respect to the object 14 and by detecting X-rays passing through the object 14 at a plurality of positions of the gantry 12.

The controller 26 may control the movement of the gantry 12 and furthermore may evaluate the acquired data from the line detectors 24 to generate the attenuation image data.

In addition, the device 10 allows the calibration of the dPCI interferometer G1, G2 to be performed in two separate steps: The common calibration of the image detector (e.g. for dark current, sensitivity) without the absorbing "analyzer" grating(s) G1 and G2, in which the source grating is preferable in the second "off" position, and the subsequent additional calibration of the dPCI interferometer G1, G2 with both gratings G1 and G2 in the first "on" position and the source grating G0 is in the second "off" position. A system with the interferometer locking into the imaging path requires a much more complex, time-consuming, and potentially less accurate combined calibration.

In step 66, the gratings G1 and G2 and optionally the source grating G0 are moved in the second "off" position and the line detector 24 is calibrated.

In step 68, the gratings G1 and G2 are moved in the first "on" position and the source grating G0 is moved in second "off" position. After that the interferometer comprising the phase grating G1 and the absorber grating G2 is calibrated.

An imaging device 10 able for both differential phase contrast imaging and attenuation imaging may have many advantages. On the one hand, differential phase contrast mammography (dPCM) is currently being explored very intensively in view of its potential benefits like increased visibility and sharpness of micro-calcifications, better tumor delineation versus healthy tissue and increased general image sharpness and quality. At the current state of research, though, it is yet unclear, whether the improved image quality will allow a dose reduction that compensates for the X-ray quanta that are lost in the absorbing part of the interferometer behind the patient. On the other hand, depending on the clinical application (screening with manual reading or with computer-assisted-diagnosis, diagnostic workup, image-guided biopsy, etc.), clinical protocols and local guidelines will require part of the mammography workload to be carried out in "conventional" setup without the post-patient interferometer (i.e. gratings G1 and G2), while other parts will benefit from the "dPCI" setup with the interferometer. While immediately obvious for the clinical approval studies themselves and the initial years after introduction of dPCI systems to the market, the need for inserting/removing the phase contrast interferometer on a scan-by-scan basis is expected to remain forever.

Furthermore, in clinical settings with a wide mix e.g. of dense vs. fatty breast or Caucasian vs. African-American vs. Asian women, a clinician will require the ability to choose on a per-patient or even per-view basis. Finally, market uptake will be faster if a clinician is not forced to choose a priori between a conventional system without dPCI or a system that can only perform dPCI, but can buy a conventional system with dPCI as an option that he can turn on or off per his clinical judgment.

As pointed out above and depending on the nature of the mammographic scan being acquired (screening or diagnostic or interventional), clinical protocols and guidelines and clinician preferences on a per-scan basis will usually require the ability to switch between conventional and phase contrast imaging, as is possible with the imaging device 10 as described above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS

G0 source grating
G1 phase grating
G2 absorber grating
10 X-ray imaging device
12 gantry
14 object
16 frame
18 support platform
20 X-ray source
22 collimator
24 line detector
26 controller
28 fan-shaped beam
30 slit
32 detector line
34 grating line
36 group of grating lines
38 transparent areas 40 motor
42 rail
44 stopper
46 position sensor
48 hinge

The invention claimed is:

1. An X-ray differential phase contrast imaging device, comprising:
an X-ray source for generating an X-ray beam;
a source grating (G0) for generating a coherent X-ray beam from a non-coherent X-ray source (20);
a collimator comprising slits for splitting the coherent X-ray beam into a plurality of fan-shaped X-ray beams for passing through an object;
a phase grating (G1) for generating an interference pattern and an absorber grating (G2) for generating a Moiré pattern from the interference pattern arranged after the object;
  a line detector comprising detector lines for detecting the Moiré pattern generated by the phase grating (G1) and the absorber grating (G2) from the fan-shaped X-ray beams (28) passing through the object;
  wherein the X-ray source, source grating (G0), collimator, phase grating (G1), absorber grating (G2) and line detector are fixed to a common gantry and are movable with respect to the object, such that a number of interference patterns from different positions of the gantry are detectable for reconstructing a differential phase image of the object;
wherein groups of grating lines and transparent areas (38) alternate with respect to each other in a direction perpendicular to the direction of the detector lines;
  wherein at least one grating (G0, G1, G2) of the source grating, the phase grating and the absorber grating comprises groups of grating lines and transparent areas between the groups of grating lines, and is movable with respect to the gantry, such that
    in a first position of the source grating (G0) the X-ray beams pass through the grating lines and subsequently pass through the slits of the collimator and in a second position of the source grating (G0) the X-ray beams pass through the transparent areas and subsequently pass through the slits of the collimator, or
    in a first position at least one of the phase grating (G1) or the absorber grating (G2) the fan-shaped X-ray beams pass through the grating lines, and in a second position at least one of the phase grating (G1) or the absorber grating (G2) the fan-shaped X-ray beams pass through the transparent areas.

2. The imaging device of claim 1,
wherein the groups of grating lines are equidistant and the transparent areas are equidistant.

3. The imaging device of claim 1,
wherein the grating (G0, G1, G2) comprises a substrate transparent for X-rays and the transparent areas comprises areas on the substrate without metallization.

4. The imaging device of claim 3,
wherein the grating lines are metal lines on the substrate; and/or
wherein the grating lines are metal-filled trenches in the substrate; and/ or
wherein the grating lines are trenches in the substrate.

5. The imaging device of claims claim 1, wherein the transparent areas (38) comprises holes in a substrate of the grating.

6. The imaging device of claim 1, further comprising:
a motor for moving the grating (G1, G2) between the first position and the second position; and
a controller for controlling the movement.

7. The imaging device claim 1,
wherein the first position of the grating (G1, G2) is determined by a mechanical stopper.

8. The imaging device claim 1,
wherein the first position of the grating (G1, G2) is determined by a position sensor.

9. The imaging device claim 1, further comprising:
rails for guiding the grating.

10. The imaging device claim 1,
wherein only the absorber grating (G2) has the transparent areas.

11. The imaging device claim 1,
wherein the phase grating (G1) and the absorber grating (G2) have the transparent areas.

12. The imaging device of claim 11,
wherein the phase grating (G1) and the absorber grating (G2) are movable independently from each other between the first position and the second position; and/or
wherein the phase grating (G1) and the absorber grating (G2) are fixedly connected with each other and are movable together between the first position and the second position.

13. The imaging device claim 1, further comprising:
a hinge for removing the source grating (G0) from the X-ray beam.

14. A method for acquiring differential phase image data and attenuation image data with the same device, the method comprising:
moving a grating (G0, G1, G2) selected from a source grating, a phase grating and an absorber grating of the device in a first position, such that fan-shaped X-ray beams generated by a collimator pass through groups of grating lines on the grating (G0, G1, G2);
acquiring differential phase image data by moving a gantry with the source grating (G0), phase grating (G1) and absorber grating (G2) and a line detector with respect to an object and by detecting X-rays passing through the object, the source grating (G0), phase grating (G1) and the absorber grating (G2) at a plurality of positions of the gantry;
moving the grating (G0, G1, G2) in a second position, such that the fan-shaped X-ray beams pass through transparent areas on the grating (G0, G1, G2); and
acquiring attenuation image data by moving the gantry with respect to the object and by detecting X-rays passing through the object at a plurality of positions of the gantry
wherein in a first position of the source grating (G0) the X-ray beams pass through the grating lines and subsequently pass through the slits of the collimator and in a second position of the source grating (G0) the X-ray beams pass through the transparent areas and subsequently pass through the slits of the collimator, or
in a first position at least one of the phase grating (G1) or the absorber grating (G2) the fan-shaped X-ray beams pass through the grating lines, and in a second position at least one of the phase grating (G1) or the absorber grating (G2) the fan-shaped X-ray beams pass through the transparent areas.

15. The method of claim 14, further comprising:
calibrating the line detector, when the absorber grating (G2) and the phase grating (G1) are in the second position; and
calibrating the phase grating (G1) and the absorber grating (G2), when the phase grating (G1) and the absorber grating (G2) are in the first position and the source grating (G0) is in the second position.

\* \* \* \* \*